US012788621B2

(12) United States Patent
Long

(10) Patent No.: US 12,788,621 B2
(45) Date of Patent: Nov. 10, 2026

(54) CRYOGENIC PHYSICAL THERAPY CABIN FOR HOME USE

(71) Applicant: Zhigang Long, Beijing (CN)

(72) Inventor: Zhigang Long, Beijing (CN)

( * ) Notice: Subject to any disclaimer, the term of this patent is extended or adjusted under 35 U.S.C. 154(b) by 642 days.

(21) Appl. No.: 18/233,468

(22) Filed: Aug. 14, 2023

(65) Prior Publication Data

US 2024/0050269 A1 Feb. 15, 2024

(30) Foreign Application Priority Data

Aug. 15, 2022 (CN) ......................... 202210972902.6

(51) Int. Cl.
*A61F 7/00* (2006.01)

(52) U.S. Cl.
CPC ............ *A61F 7/0053* (2013.01); *A61F 7/007* (2013.01)

(58) Field of Classification Search
CPC .......... A61F 7/0053; A61F 7/007; A61F 7/00; A61F 2007/0056; A61F 2007/0086; A61F 2007/0093; A61F 2007/0094; A61F 2007/0095; A61F 2007/0096
See application file for complete search history.

(56) References Cited

U.S. PATENT DOCUMENTS 10,271,986 B1 * 4/2019 Guertin ................. A61F 7/0053
2015/0094702 A1 4/2015 Shuppo
2015/0328432 A1 * 11/2015 Liu ........................ A61G 10/00 600/27
2019/0083298 A1 * 3/2019 Starkweather ..... A61B 18/0218
2019/0216637 A1 7/2019 Sierra Murillo
2019/0392266 A1 * 12/2019 Zhong ..................... G10L 15/22
2022/0062031 A1 * 3/2022 Geurtin .............. A61H 33/6068

FOREIGN PATENT DOCUMENTS

CN 207173233 U * 4/2018
CN 108491706 A * 9/2018 ........... G06F 18/214
CN 108852608 A * 11/2018 ............... A61F 7/00
CN 208636903 U * 3/2019
CN 109568055 A * 4/2019 ............. A61G 10/02
CN 111220213 A * 6/2020 ............. G01D 21/02
(Continued)

*Primary Examiner* — Emmanuel E Duke
(74) *Attorney, Agent, or Firm* — Bret E. Field; Bozicevic, Field & Francis LLP

(57) ABSTRACT

A cryogenic physical therapy cabin for home use includes a thermal insulation cabin body, an electronically controlled cabin door, a sensing module, a refrigeration apparatus, a heating apparatus and a programmable controller, wherein the sensing module, the refrigeration apparatus and the heating apparatus are arranged inside the thermal insulation cabin body, and the programmable controller is electrically connected with the sensing module, the refrigeration apparatus, the heating apparatus and the electronically controlled cabin door respectively; the sensing module acquires sensing data and sends the sensing data to the programmable controller which controls opening and closing of the electronically controlled cabin door based on an operation instruction issued by a first user and/or the sensing data, and controls the refrigeration apparatus to perform refrigeration operation and controls the heating apparatus to perform a heating operation based on the sensing data.

7 Claims, 6 Drawing Sheets

(56) References Cited

FOREIGN PATENT DOCUMENTS

| | | | | | |
|---|---|---|---|---|---|
| CN | 112315701 | A | | 2/2021 | |
| CN | 112631230 | A | * | 4/2021 | ......... G05B 19/4184 |
| CN | 112843485 | A | | 5/2021 | |
| CN | 115177429 | A | | 10/2022 | |
| CN | 115223300 | A | | 10/2022 | |
| CN | 115252273 | A | | 11/2022 | |
| CN | 219307110 | U | | 7/2023 | |
| KR | 20170011266 | A | | 2/2017 | |
| KR | 101998179 | B1 | | 7/2019 | |
| WO | WO2020260347 | A1 | | 12/2020 | |

* cited by examiner

CRYOGENIC PHYSICAL THERAPY CABIN FOR HOME USE

TECHNICAL FIELD

The present invention relates to the field of cryogenic physical therapy, in particular to a cryogenic physical therapy cabin for home use.

BACKGROUND

With the accelerated pace of modern life, more and more people are in sub-health state, and long-term exposure to sub health is extremely detrimental to human health. As a new physical therapy technology, cryogenic physical therapy technology is gradually entering public eye from the traditional medical field. The cryogenic physical therapy is to keep human body in an extremely low-temperature (usually below −110° C.) environment for a period of time, such as for about 2-3 minutes. Endorphins are released from the user's body by stimulating user's skin at a low temperature, thus achieving functional effects of accelerating blood circulation, continuously burning fat, increasing skin elasticity and eliminating muscle fatigue and so on.

A temperature of the environment in which users are undergoing cryogenic physical therapy is extremely low. If users lose consciousness or deliberately prolongs the physical therapy time during the physical therapy, extremely low temperature will bring significant harm to users. Therefore, a commonly used cryogenic physical therapy device is placed in places with staff on duty, and the staff can operate the cryogenic physical therapy device and assist users in cryogenic physical therapy. Therefore, the commonly used cryogenic physical therapy device cannot be operated by a single user, and is difficult to enter the general home and cannot meet the home use needs of users.

SUMMARY

The purpose of embodiments of the present invention is to provide a cryogenic physical therapy cabin for home use, so as to support to be operated by a single user and further meet home cryogenic physical therapy needs of the user. The specific technical solutions are as follows.

An embodiment of the present invention provides a cryogenic physical therapy cabin for home use, wherein the cryogenic physical therapy cabin includes a thermal insulation cabin body, an electronically controlled cabin door, a sensing module, a refrigeration module, a heating module and a programmable controller, wherein:

- the sensing module, the refrigeration module and the heating module are arranged inside the thermal insulation cabin body, and the programmable controller is electrically connected with the sensing module, the refrigeration module, the heating module and the electrically controlled cabin door respectively;
- the sensing module is configured to acquire sensing data and send the sensing data to the programmable controller; and
- the programmable controller is configured to control opening and closing of the electronically controlled cabin door based on an operation instruction issued by a first user and/or the sensing data; and the programmable controller is further configured to control the refrigeration module to perform a refrigeration operation and control the heating module to perform a heating operation based on the sensing data.

Optionally, the cryogenic physical therapy cabin further includes an embedded single-chip microcomputer, which includes a single-chip microcomputer chip and an identification module, wherein:

- the single-chip microcomputer chip is electrically connected with the identification module and the programmable controller respectively;
- the identification module is configured to acquire biometric information of a user; and the single-chip microcomputer chip is configured to generate a cabin door opening signal when determining that the biometric information matches pre-stored feature information, and send the cabin door opening signal to the programmable controller; and
- the programmable controller is configured to control the electronically controlled cabin door to be opened when receiving the cabin door opening signal.

Optionally, the cryogenic physical therapy cabin further includes a variable wind module, which is electrically connected with the programmable controller, and the embedded single-chip microcomputer further includes a network module, wherein the single-chip microcomputer chip is electrically connected with the network module and the programmable controller respectively, and the network module establishes a communication connection with a first user device;

- the network module is configured to acquire first operation information input by a second user via the first user device, and send the first operation information to the single-chip microcomputer chip, wherein the first operation information includes at least one of start time, temperature and wind speed;
- the single-chip microcomputer chip is configured to generate a first control instruction based on the first operation information and send the first control instruction to the programmable controller; and
- the programmable controller is configured to control a target component in the cryogenic physical therapy cabin to perform an operation indicated by the first control instruction when receiving the first control instruction, wherein the target component includes at least one of the refrigeration module, the heating module, the electrically controlled cabin door and the variable wind module.

Optionally, the network module establishes a communication connection with a second user device;

- the programmable controller is further configured to determine whether an abnormal situation occurs in the cryogenic physical therapy cabin based on a device state of the cryogenic physical therapy cabin, and send abnormal information to the single-chip microcomputer chip if the abnormal situation occurs in the cryogenic physical therapy cabin; and
- the single-chip microcomputer chip is configured to generate a prompt message based on the abnormal information and send the prompt message to the second user device through the network module.

Optionally, the cryogenic physical therapy cabin further includes an air pressure balance pipe, and the air pressure balance pipe connects an internal environment with an external environment of the thermal insulation cabin body; and

- the air pressure balance pipe is configured to maintain air pressure inside the thermal insulation cabin body within a preset pressure range when the air pressure inside the thermal insulation cabin body changes.

Optionally, the cryogenic physical therapy cabin further includes a safety module, wherein the safety module comprises an emergency button, and the emergency button is arranged inside the thermal insulation cabin body and/or outside the thermal insulation cabin body; the emergency button is electrically connected with the programmable controller; and the programmable controller is further configured to receive an emergency signal generated when the emergency button is triggered, and perform at least one of: controlling the refrigeration module to stop refrigeration, controlling the heating module to start heating, and controlling the electronically controlled cabin door to be opened.

Optionally, the safety module further includes a display screen, wherein the display screen is arranged inside the thermal insulation cabin body, and a surface of the display screen is provided with thermal insulation glass, and the display screen is electrically connected with the programmable controller; and the programmable controller is configured to control the display screen to display safety prompt information when receiving the emergency signal.

Optionally, the sensing module includes a camera, a temperature sensor, a human body sensor and a timer;

the camera is configured to acquire a monitoring video inside the thermal insulation cabin body and send the monitoring video to the programmable controller; the temperature sensor is configured to acquire temperature data inside the thermal insulation cabin body and send the temperature data to the programmable controller; the human body sensor is configured to detect human body data inside the thermal insulation cabin body and send the human body data to the programmable controller;

the programmable controller is configured to send the monitoring video to a third user device and/or control a target display device to play the monitoring video;

the programmable controller is further configured to control the timer to start timing when determining that there is a person inside the thermal insulation cabin body based on the human body data, and control the electronically controlled cabin door to be closed when determining that there is no person inside the thermal insulation cabin body based on the human body data; and the programmable controller is further configured to perform, when determining that a temperature inside the thermal insulation cabin body is lower than a preset threshold based on the temperature data or when timing duration of the timer reaches a preset duration, at least one of controlling the refrigeration module to stop refrigeration, controlling the heating module to start heating, and controlling the electronically controlled cabin door to be opened The beneficial effects of the embodiments of the present invention are as follows:

the cryogenic physical therapy cabin provided by the embodiment of the present invention includes a thermal insulation cabin body, an electronically controlled cabin door, a sensing module, a refrigeration module, a heating module and a programmable controller, wherein the sensing module, the refrigeration module and the heating module are arranged inside the thermal insulation cabin body, and the programmable controller is electrically connected with the sensing module, the refrigeration module, the heating module and the electronically controlled cabin door respectively; the sensing module is configured to acquire sensing data and send the sensing data to the programmable controller; the programmable controller is configured to control the opening and closing of the electronically controlled cabin door based on an operation instruction issued by a first user and/or the sensing data; the programmable controller is further configured to control the refrigeration module to perform a refrigeration operation and control the heating module to perform a heating operation based on the sensing data. It can be seen that during the cryogenic physical therapy of the user, the programmable controller can control the cryogenic physical therapy cabin based on the operation instruction and/or the sensing data, so that there is no need for staff to operate the cryogenic physical therapy cabin and assist the user in the cryogenic physical therapy. The cryogenic physical therapy cabin supports to be operated by the single user and can meet the home cryogenic physical therapy needs of the user. Of course, it is not necessary to achieve all the advantages mentioned above at the same time for any product or method of the present invention.

BRIEF DESCRIPTION OF THE DRAWINGS

In order to more clearly describe the technical solutions of the embodiments of the present invention and the prior art, accompanying drawings that need to be used in the embodiments and the prior art will be briefly described below. Obviously, accompanying drawings described below are for only some of embodiments of the present invention. Those skilled in the art may also obtain other embodiments based on these accompanying drawings.

FIG. 6(*b*) is a schematic diagram of another specific structure of the security module based on the embodiment shown in FIG. 1;

FIG. 6(*c*) is a schematic diagram of yet another specific structure of the security module based on the embodiment shown in FIG. 1;

DETAILED DESCRIPTION

In the following, the technical solutions in the embodiments of the invention will be clearly and completely described with reference to the accompanying drawings. Obviously, the described embodiments are only some, and not all, of the embodiments of the invention. All other embodiments obtained based on the embodiments of the invention by those skilled in the art fall into the scope of protection of the invention.

In order to enable the cryogenic physical therapy device to be operated by a single user and further meet home cryogenic physical therapy needs of the user, an embodiment of the present invention provides a cryogenic physical therapy cabin. The cryogenic physical therapy cabin provided by the embodiment of the present invention will be described below.

Figure 1:
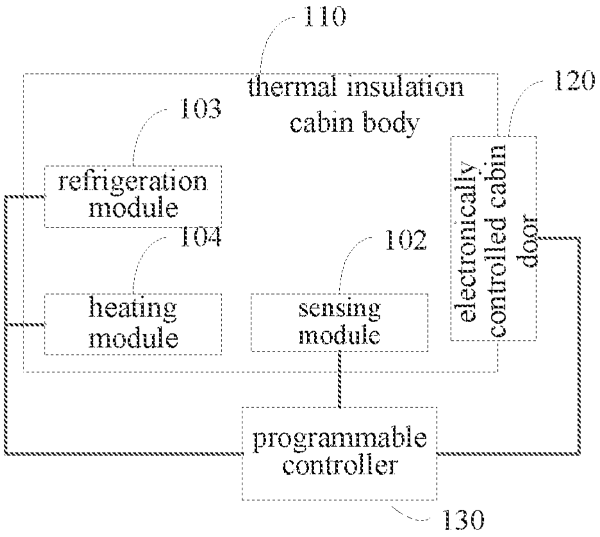
FIG. 1 is a schematic structure diagram of a cryogenic physical therapy cabin for home use provided by an embodiment of the present invention.

FIG. 1 shows the cryogenic physical therapy cabin for home use, which includes a thermal insulation cabin body 110, an electrically controlled cabin door 120, a sensing module 102, a refrigeration module 103, a heating module 104 and a programmable controller 130, wherein:

- the sensing module 102, the refrigeration module 103 and the heating module 104 are arranged inside the thermal insulation cabin body 110, and the programmable controller 130 is electrically connected with the sensing module 102, the refrigeration module 103, the heating module 104 and the electrically controlled cabin door 120 respectively;
- the sensing module 102 is configured to acquire sensing data and send the sensing data to the programmable controller 130;
- the programmable controller 130 is configured to control opening and closing of the electronically controlled cabin door 120 based on an operation instruction issued by a first user and/or the sensing data; the programmable controller 130 is further configured to control the refrigeration module 103 to refrigerate and control the heating module 104 to heat based on the sensing data.

It can be seen that the cryogenic physical therapy cabin provided by the embodiment of the present invention includes a thermal insulation cabin body, an electronically controlled cabin door, a sensing module, a refrigeration module, a heating module and a programmable controller, wherein the sensing module, the refrigeration module and the heating module are arranged inside the thermal insulation cabin body, and the programmable controller is electrically connected with the sensing module, the refrigeration module, the heating module and the electronically controlled cabin door respectively; the sensing module is configured to acquire sensing data and send the sensing data to the programmable controller; the programmable controller is configured to control the opening and closing of the electronically controlled cabin door based on an operation instruction issued by a first user and/or the sensing data; the programmable controller is further configured to control the refrigeration module to perform a refrigeration operation and control the heating module to perform a heating operation based on the sensing data. It can be seen that during the cryogenic physical therapy of the user, the programmable controller can control the cryogenic physical therapy cabin based on the operation instruction and/or the sensing data, so that there is no need for staff to operate the cryogenic physical therapy cabin and assist the user in the cryogenic physical therapy. The cryogenic physical therapy cabin supports to be operated by the single user and can meet the home cryogenic physical therapy needs of the user.

In the above-mentioned cryogenic physical therapy cabin for home use, the thermal insulation cabin body 110 is a cabin body of the cryogenic physical therapy cabin made of thermal insulation materials. The thermal insulation cabin body 110 is hollow, and its external shape can be cubic, egg-shaped, irregular, etc., which is not specifically limited here. The thermal insulation cabin body 110 is provided with an electrically controlled cabin door 120. When the electrically controlled cabin door 120 is opened, air inside and outside the cryogenic physical therapy cabin can circulate, that is, temperatures inside and outside the cryogenic physical therapy cabin can be the same. When the electronically controlled cabin door 120 is closed, the interior of the cryogenic physical therapy cabin can be isolated from external environment, so that the temperature inside the cryogenic physical therapy cabin can be maintained for a long time, and at this time, the temperature of internal environment the cryogenic physical therapy cabin can be reduced, for example, to below −110° C. to meet the cryogenic physical therapy needs of users. In an implementation, a silicone sealing strip can also be arranged at a joint between the electrically controlled cabin door 120 and the thermal insulation cabin body 110, which can, when the electrically controlled cabin door 120 is closed, enhance thermal insulation and sealing effect of the thermal insulation cabin body 110, reduce energy exchange between the inside and the outside of the cryogenic physical therapy cabin, and reduce energy consumption of cryogenic physical therapy.

The sensing module 102, the refrigeration module 103 and the heating module 104 can be arranged inside the thermal insulation cabin body 110. The sensing module 102 can be configured to acquire sensing data, and the programmable controller 130 is electrically connected with the sensing module 102, and then the sensing module 102 can send the acquired sensing data to the programmable controller 130. The sensing module 102 may include various types of sensing devices and apparatus, such as a temperature sensor, a humidity sensor, a human body sensor, a timer, a camera, etc., which are not specifically limited here. The sensing data is data of the internal environment of the thermal insulation cabin body 110 acquired by the sensing module 102, which can include data such as temperature data acquired by the temperature sensor, humidity data acquired by the humidity sensor, human body data detected by the human body sensor, monitoring video of the interior of the thermal insulation cabin body 110 acquired by the camera, and duration of cryogenic physical therapy acquired by the timer, etc.

The programmable controller 130 is a control apparatus of the cryogenic physical therapy cabin, and can be preprogrammed before the cryogenic physical therapy cabin leaves the factory, such that the programmable controller 130 can execute the instructions for storage, logical operation, sequence control, timing, counting and arithmetic operation and so on, and control other components connected with it via input and output interfaces. After acquiring the sensing data, the programmable controller 130 can control individual components in the cryogenic physical therapy cabin based on the sensing data.

Before, during and after the first user has the cryogenic physical therapy through the cryogenic physical therapy cabin, the first user can send operation instructions to the cryogenic physical therapy cabin, which may include setting the time of cryogenic physical therapy, adjusting the temperature of cryogenic physical therapy, controlling the opening or closing of the electrically controlled cabin door, and adjusting a wind speed and so on. The programmable controller 130 is electrically connected with the electronically controlled cabin door 120, and can receive the operation instruction issued by the first user and control the opening and closing of the electronically controlled cabin door 120 based on the operation instruction and/or the sensing data.

The refrigeration module 103 is an apparatus for reducing the temperature inside the cryogenic physical therapy cabin, which can provide the first user with the extremely low-temperature environment required for cryogenic physical therapy. The refrigeration mode of the refrigeration module 301 may be various, for example, the refrigeration module 301 can refrigerate by using electric energy and using a compressor for charging refrigerant, and can also refrigerate through liquid nitrogen vaporization, which is not specifically limited here, as long as the refrigeration module 301 can provide the extremely low-temperature environment required for cryogenic physical therapy. In one implementation, when the temperature of the cryogenic physical therapy cabin is reduced by the evaporative refrigeration of charging refrigerant with a compressor, the evaporator can be used as the refrigeration module 103, and can further be arranged inside the cryogenic physical therapy cabin. Other parts (such as compressors, refrigerants, etc.) can be arranged outside the cryogenic physical therapy cabin.

The heating module 104 can rapidly increase the temperature inside the cryogenic physical therapy cabin to reduce the risk of frostbite of the first user during the cryogenic physical therapy, and can also be used for defrosting the interior of the cryogenic physical therapy cabin, thereby improving the refrigeration efficiency. The programmable controller 130 is electrically connected with the refrigeration module 103 and the heating module 104, and further the programmable controller 130 can control the refrigeration module 103 to refrigerate and control the heating module 104 to heat based on the sensing data.

In the solution provided by the embodiment of the present invention, the first user can send an operation instruction to preset parameters such as the temperature, start time, duration and the like of the cryogenic physical therapy before using the cryogenic physical therapy cabin for cryogenic physical therapy. Therefore, after the current time reaches the start time of the cryogenic physical therapy set by the first user, the programmable controller 130 can control the electronically controlled cabin door 120 to be opened, and control, after determining that the first user enters the cryogenic physical therapy cabin based on the received sensing data acquired by the sensing module 102, the electronically controlled cabin door 120 to be closed, and then control the refrigeration module 103 to refrigerate until the temperature within the thermal insulation cabin body reaches the temperature of the cryogenic physical therapy preset by the first user.

During the cryogenic physical therapy, the first user can continue to issue operation instructions to cause the programmable controller 130 to control the opening of the electronically controlled cabin door 120, change the temperature, wind speed, physical therapy duration, etc., so that the first user can open the electronically controlled cabin door 120 in time and quickly increase the temperature when feeling unwell so as to avoid frostbite; the programmable controller 130 can also continuously receive the sensing data acquired by the sensing module 102, so as to determine whether the temperature of the environment in which the first user is located has not met the temperature requirement for cryogenic physical therapy, whether the temperature of the environment is too low, whether the duration of the cryogenic physical therapy is too long, etc., and control individual components of the cryogenic physical therapy cabin to adjust the process of the cryogenic physical therapy. For example, the programmable controller 130 can control the heating module 104 to heat to increase the temperature; and control the electrically controlled cabin door 120 to be opened to end the cryogenic physical therapy in advance and so on, so as to further improve the safety of the cryogenic physical therapy process.

After the first user completes the cryogenic physical therapy, the first user leaves the cryogenic physical therapy cabin, and can issue an operation instruction to enable the programmable controller 130 to control the electronically controlled cabin door 120 to be closed. The programmable controller 130 can also control the electronically controlled cabin door 120 to be closed when determining that there is no user in the cryogenic physical therapy cabin based on the received sensing data acquired by the sensing module 102, so as to prevent strangers or children from accidentally entering the cryogenic physical therapy cabin, which can cause danger. In an implementation, the programmable controller 130 can control the heating module 104 to heat when determining that the refrigeration efficiency is low based on the received sensing data acquired by the sensing module 102. For example, when the temperature sensor in the sensing module 102 senses that the temperature of the evaporator is low, but the internal environment of the cryogenic physical therapy cabin is cooling slowly, the heating module 104 can heat the evaporator to remove the frost on a surface of the evaporator, so as to improve the cooling efficiency.

It can be seen that in the cryogenic physical therapy cabin for home use, the sensing module can acquire the sensing data and send the sensing data to the programmable controller, and the programmable controller can control the opening and closing of the electrically controlled cabin door based on the operation instruction issued by the first user and/or the sensing data; the programmable controller can also control the refrigeration module to perform a refrigeration operation and control the heating module to perform a heating operation based on the sensing data. Therefore, with the operation instruction issued by the user and the sensing data acquired by the sensing module, there is no need for staff to operate the cryogenic physical therapy cabin and assist the user in cryogenic physical therapy. The cryogenic physical therapy cabin can intelligently control the user's cryogenic physical therapy process, reduce the frostbite risk of the user, support to be operated by the single user, and meet the home cryogenic physical therapy needs of the user.

Figure 2:
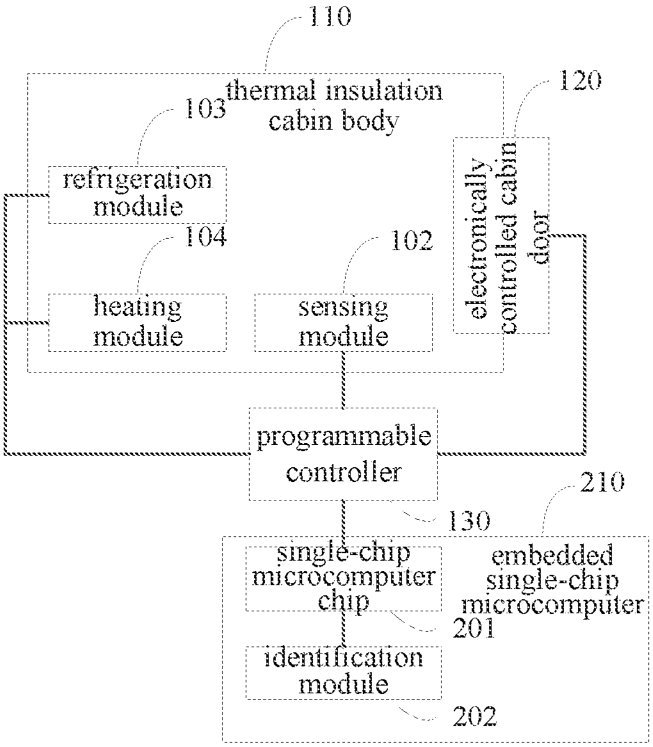
FIG. 2 is a schematic diagram of a specific structure of the cryogenic physical therapy cabin for home use based on the embodiment shown in FIG. 1.

As an implementation of the embodiment of the present invention, as shown in FIG. 2, the cryogenic physical therapy cabin may further include an embedded single-chip microcomputer 210, which may include a single-chip microcomputer chip 201 and an identification module 202, wherein the single-chip microcomputer chip 201 is electrically connected with the identification module 202 and the programmable controller 130 respectively; the identification module 202 is configured to obtain biometric information of a user; the single-chip microcomputer chip 201 is configured to generate a cabin door opening signal when it is determined that the biometric information matches pre-stored feature information, and send the cabin door opening signal to the programmable controller 130; the programmable controller 130 is configured to control the electronically controlled cabin door 120 to be opened when receiving the cabin door opening signal.

As an implementation, the cryogenic physical therapy cabin also includes an embedded single-chip microcomputer 210, which includes a single-chip microcomputer chip 201 and an identification module 202, and the single-chip microcomputer chip 201 is electrically connected with the identification module 202 and the programmable controller 130 respectively. In the solution provided by the embodiment of the present invention, the embedded single-chip microcomputer 210 is a system for user identification. The identification module 202 can acquire the biometric information of the user. For example, the identification module can include a face device module to acquire facial feature information of the user; and can further include a fingerprint device module to acquire fingerprint feature information of the user; and can further include an iris recognition module to acquire iris feature information of the user, etc., which is not specifically limited here.

In an implementation, the identification module 202 can further include a password identification function to identify password information preset by the user; and can further include an IC (Integrated Circuit) card identification function to identify an IC card corresponding to the cryogenic physical therapy cabin; and can further include RDFI (Radio Frequency Identification) function to identify a radio frequency information tag of the user, etc.

The single-chip microcomputer chip 201 can store the feature information and determine whether the biometric information of the user acquired by the identification module 202 matches the pre-stored feature information. In an implementation, when each user uses the cryogenic physical therapy cabin for the first time, the biometric information of the user can be acquired through the identification module 202, and the biometric information and an identity of the user can be registered and stored in the single-chip microcomputer chip 201 correspondingly. Further, a cryogenic physical therapy scheme corresponding to each user can be preset respectively, which can better meet cryogenic physical therapy needs for different users in the home.

If the biometric information of the user acquired by the identification module 202 matches the pre-stored feature information in the microcomputer chip 201, the microcomputer chip 201 can generate a cabin door opening signal and send the cabin door opening signal to the programmable controller 130, so that the programmable controller 130 can control the electronically controlled cabin door 120 to be opened when receiving the cabin door opening signal. If the biometric information of the user does not match the pre-stored feature information, the electronically controlled cabin door 120 will not be opened. Thereby further reducing a probability that unregistered strangers or children mistakenly enter the cryogenic physical therapy cabin.

It can be seen that in the embodiment, when the biometric information of the user acquired by the identification module matches the pre-stored feature information in the single-chip microcomputer chip, the single-chip microcomputer chip can generate a cabin door opening signal and send the cabin door opening signal to the programmable controller, so that the programmable controller can control the electronically controlled cabin door to be opened when receiving the cabin door opening signal. Therefore, the risk that unregistered strangers or children mistakenly enter the low-temperature physical therapy cabin is further reduced, and the cryogenic physical therapy needs of different users in the home can be better meet by presetting the cryogenic physical therapy scheme for each user.

Figure 3:
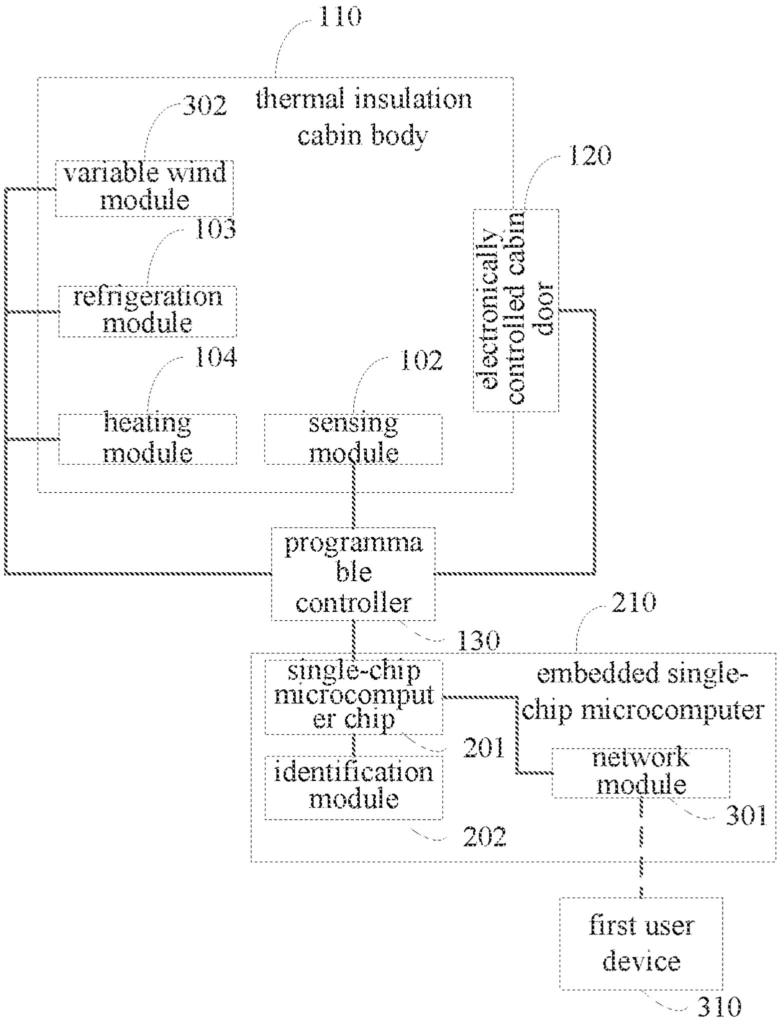
FIG. 3 is a schematic diagram of a specific structure of an embedded single-chip microcomputer based on the embodiment shown in FIG. 2.

As an implementation of the embodiment of the present invention, as shown in FIG. 3, the cryogenic physical therapy cabin may further include a variable wind module 302, which is electrically connected with the programmable controller 130, and the embedded single-chip microcomputer 210 may further include a network module 301, wherein the single-chip microcomputer chip 201 is electrically connected with the network module 301 and the programmable controller 130 respectively, and the network module 301 establishes a communication connection with a first user device 310. The network module 301 is configured to acquire first operation information input by a second user via the first user device 310, and send the first operation information to the single-chip microcomputer chip 201, wherein the first operation information includes at least one of start time, temperature and wind speed; the single-chip microcomputer chip 201 is configured to generate a first control instruction based on the first operation information and send the first control instruction to the programmable controller 130; the programmable controller 130 is configured to control a target component in the cryogenic physical therapy cabin to perform an operation indicated by the first control instruction when receiving the first control instruction, wherein the target component includes at least one of the refrigeration module 103, the heating module 104, the electrically controlled cabin door 120 and the variable wind module 302.

In order to control the wind speed inside the cryogenic physical therapy cabin, the cryogenic physical therapy cabin can also include a variable wind module 302, which is configured to control the air flow in the cryogenic physical therapy cabin. The faster the air flow speed is, the lower the apparent temperature of the user is. Therefore when the temperature is slightly higher, it is not necessary to spend a lot of energy on refrigeration through the refrigeration module 103, and the apparent temperature of the user can be reduced by increasing the wind speed of the variable wind module 302; the variable wind module 302 can also control a direction of air flow to enable different parts of the user's body to feel different temperatures, which can better meet the cryogenic physical therapy needs of the user, because the sensitivity of different parts of the user's body to low temperature is different.

For example, when the refrigeration module 103 reduces the temperature of the cryogenic physical therapy cabin by the evaporative refrigeration of charging refrigerant with a compressor, the variable wind module 302 can be connected with the evaporator to form a sealed air flow channel with an air inlet on one side and an air outlet on the other side. The variable wind module 302 can include an adjustable speed motor, fan blades and an air outlet with adjustable wind direction. When there is a significant fluctuation in the temperature inside the cabin, such as when the temperature inside the cabin is high, the speed of the speed-regulating fan can be increased, and in the contrast, when the temperature inside the cabin is low, the speed of the speed-regulating fan can be reduced, thus achieving a stable cryogenic physical therapy effect.

The embedded single-chip microcomputer 210 also includes a network module 301, which can be used for information transmission between the cryogenic physical therapy cabin and other external components. In the solution provided by the embodiment of the present invention, the network module 301 can establish a communication connection with the first user device 310, wherein a mode of the communication connection can be 4G network connection, 5G network connection, and WIFI (Wireless Fidelity) connection, etc., which is specifically limited here. The first user device 310 can be configured to remotely configure the cryogenic physical therapy cabin. For example, the first user device 310 can be a computer or a server installed with a remote client of the cryogenic physical therapy cabin, and mobile phones, tablet computers and intelligent devices, etc. installed with a software application corresponding to the cryogenic physical therapy cabin, which is not specifically limited here.

The second user can input the first operation information via the first user device 310, and the second user can be the above first user who has the cryogenic physical therapy or other users in the home. The first operation information input by the second user via the first user device 310 may include at least one of physical therapy start time, physical therapy temperature and wind speed.

The network module 301 can acquire the first operation information input by the second user via the first user device, and send the first operation information to the single-chip microcomputer chip 201. The single-chip microcomputer chip 201 can generate a first control instruction based on the first operation information and send the first control instruction to the programmable controller 130. Further, the programmable controller 130 can receive the first control instruction and control the target component in the cryogenic physical therapy cabin to perform an operation indicated by the first control instruction. The target component can include the refrigeration module 103, the heating module 104, the electrically controlled cabin door 105, and the variable wind module 302, etc.

For example, there are two users who use the cryogenic physical therapy cabin in a home, namely user A and user B. User A is the first user and user B is the second user. When user A returns home from work, user A can issue an operation instruction to the programmable controller of the cryogenic physical therapy cabin and enter the cryogenic physical therapy cabin for cryogenic physical therapy. At this time, user B has not returned home yet. User B can input operation information through a software application of a mobile phone pre-bound with the cryogenic physical therapy cabin, and the mobile phone can send the operation information to the single-chip microcomputer chip of the cryogenic physical therapy cabin, wherein the operation information includes the physical therapy start time and the physical therapy temperature. Then when user A finishes the cryogenic physical therapy, the single-chip microcomputer chip can generate a control instruction based on the operation information and send the control instruction to the programmable controller. When the current time reaches the preset physical therapy start time and after the user B returns home, the identification module can acquire the biometric information of the user B. When the single-chip microcomputer chip determines that the biometric information matches the pre-stored feature information, the programmable controller can control the electronically controlled cabin door to be opened, and after the user B enters the cryogenic physical therapy cabin and closes the cabin door, the programmable controller controls the refrigeration module to perform a refrigeration operation until the temperature inside the cryogenic physical therapy cabin reaches the physical therapy temperature preset by the user B.

It can be seen that in the embodiment, the cryogenic physical therapy cabin can further include the variable wind module, and the embedded single-chip microcomputer can further include the network module, which can acquire the first operation information input by the second user via the first user device and send the first operation information to the single-chip microcomputer chip. The single-chip microcomputer chip can generate the first control instruction based on the first operation information and send the first control instruction to the programmable controller. The programmable controller can then receive the first control instruction and control the target component in the cryogenic physical therapy cabin to perform the operation indicated by the first control instruction. Therefore, the user does not need to operate the cryogenic physical therapy cabin on site, and can control the cryogenic physical therapy cabin through the first user device and the network module, so that the cryogenic physical therapy needs of the user can be met more timely.

Figure 4:
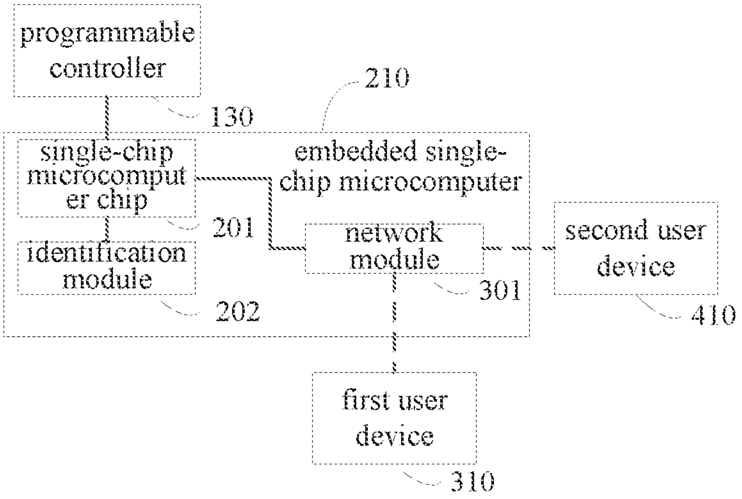
FIG. 4 is a schematic diagram of another specific structure of the embedded single-chip microcomputer based on the embodiment shown in FIG. 3.

As an implementation of the embodiment of the present invention, as shown in FIG. 4, the network module 301 may establish a communication connection with a second user device 410; the programmable controller 130 is further configured to determine whether an abnormal situation occurs in the cryogenic physical therapy cabin based on a device state of the cryogenic physical therapy cabin, and send abnormal information to the single-chip microcomputer chip 201 if the abnormal situation occurs in the cryogenic physical therapy cabin; the single-chip microcomputer chip 201 is configured to generate a prompt message based on the abnormal information and send the prompt message to the second user device 410 through the network module 301.

The network module 301 can also establish a communication connection with the second user device 410, which can be an intelligent device of the user's emergency contact, such as a portable electronic device such as a mobile phone, or can be an alarm device of a manufacturer of the cryogenic physical therapy cabin for detecting the device state of the cryogenic physical therapy cabin, which is not specifically limited here.

The programmable controller 130 can acquire device state information of the cryogenic physical therapy cabin, which can include the sensing data of the internal environment of the cryogenic physical therapy cabin acquired by the sensing module 102, such as temperature data, humidity data, human body data, monitoring video, cryogenic physical therapy duration and other data, and can also include device information of the cryogenic physical therapy cabin, such as location information of the cryogenic physical therapy cabin, device usage times, device failure information and other information, which is not specifically limited here. The programmable controller 130 can determine whether an abnormal situation occurs in the cryogenic physical therapy cabin based on the device state information. The abnormal situation may include that the user has been in the cryogenic physical therapy cabin for too long, the electronically controlled cabin door of the cryogenic physical therapy cabin cannot be opened, and a circuit of the cryogenic physical therapy cabin is faulty, which is not specifically limited here.

If it is determined that the abnormal situation occurs in the cryogenic physical therapy cabin, the programmable controller 130 can send the abnormal information to the single-chip microcomputer chip 201, and the single-chip microcomputer chip 201 can generate a prompt message based on the abnormal information and send the prompt message to the second user device 410 through the network module 301. For example, when the abnormal situation is that the electronically controlled cabin door of the cryogenic physical therapy cabin cannot be opened and there is no user in the cryogenic physical therapy cabin, the programmable controller 130 can send the abnormal information of the electronically controlled cabin door to the single-chip microcomputer chip 201, and the single-chip microcomputer chip 201 can generate a maintenance diagnostic message based on the abnormal information, and send the maintenance diagnostic message to the alarm device of the manufacturer of the cryogenic physical therapy cabin via the network module 301, so that the manufacturer can arrange the staff for maintenance based on the location information of the cryogenic physical therapy cabin included in the maintenance diagnostic message. For another example, when the abnormal situation is that the user has been in the cryogenic physical therapy cabin for too long, the network module 301 can send a corresponding prompt message to the intelligent device of the emergency contact and the alarm device of the manufacturer of the cryogenic physical therapy cabin, so that the emergency contact can quickly check whether an abnormal situation occurs for the user who is using the cryogenic physical therapy cabin, and the manufacturer can remotely force the cryogenic physical therapy cabin to be closed.

It can be seen that, in the embodiment, the network module can establish a communication connection with the second user device, and the programmable controller can also send abnormal information to the single-chip microcomputer chip when determining that the abnormal situation occurs in the cryogenic physical therapy cabin based on the device state of the cryogenic physical therapy cabin, and the single-chip microcomputer chip can generate a prompt message based on the abnormal information and send the prompt message to the second user device through the network module. Therefore, the manufacturer can be notified when the cryogenic physical therapy cabin needs maintenance, and the emergency contact and the manufacturer can be notified when the user is in danger, so as to quickly solve the danger, thus improving the safety of cryogenic physical therapy.

Figure 5:
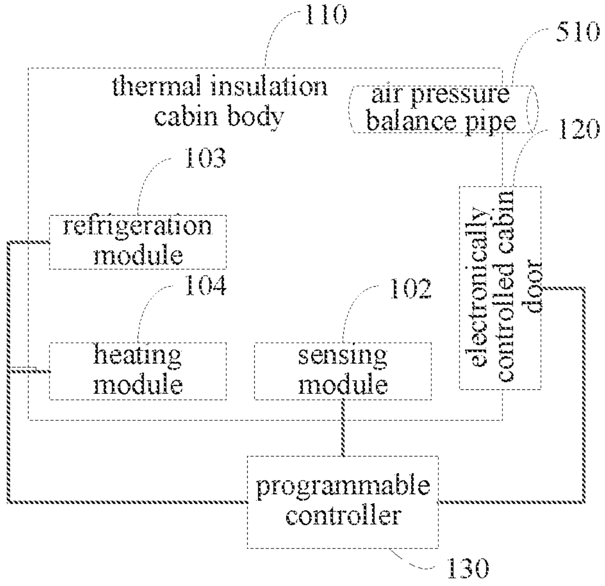
FIG. 5 is a schematic diagram of a configuration of an air pressure balance pipe of the cryogenic physical therapy cabin based on the embodiment shown in FIG. 1.

As an implementation of the embodiment of the present invention, as shown in FIG. 5, the cryogenic physical therapy cabin may further include an air pressure balance pipe 510, which is connected the internal environment with external environment of the thermal insulation chamber 110; the air pressure balance pipe 510 is configured to maintain air pressure inside the thermal insulation cabin body 110 within a preset pressure range when the air pressure inside the thermal insulation cabin body 110 changes.

Because air expands with heat and contracts with cold, cold air in the cryogenic physical therapy cabin will be quickly discharged to the external environment every time the electronically controlled cabin door 120 is opened. Upon the electronically controlled cabin door 120 is closed again, the temperature of hot air that just entered the cryogenic physical therapy cabin decreases rapidly, and thus volume of the hot air decreases sharply, resulting in the decrease of air pressure in the cryogenic physical therapy cabin. For example, when the temperature in the cryogenic physical therapy cabin reaches −120° C., the air pressure inside the cryogenic physical therapy cabin is only half of that of the external environment, and such rapid change of air pressure will pose a significant threat to the safety of users.

In an implementation, the cryogenic physical therapy cabin further includes an air pressure balance pipe 510, which connects the internal environment with external environment of the thermal insulation cabin body 110. After each opening and closing of the electronically controlled cabin door 120, the air pressure inside the cryogenic physical therapy cabin decreases, and the air pressure balance pipe 510 can be opened, so that air in the external environment of the cryogenic physical therapy cabin can enter the interior of the cryogenic physical therapy cabin through the air pressure balance pipe 510. As the temperature inside the cryogenic physical therapy cabin gradually decreases and a balance between the air pressure in the internal environment and the air pressure in the external environment is achieved, the air pressure balance pipe 510 can be closed, so as to isolate the gas exchange between the internal and external environment of the cryogenic physical therapy cabin and play a function of heat preservation.

Therefore, the air pressure balance pipe 510 can maintain the air pressure inside the thermal insulation cabin body 110 within the preset pressure range when the air pressure inside the thermal insulation cabin body 110 changes. The preset pressure range can be an air pressure range in the internal environment of the thermal insulation cabin body 110 at the preset physical therapy temperature of cryogenic physical therapy.

It can be seen that, in the embodiment, the air pressure balance pipe can connect the internal environment with external environment of the thermal insulation cabin body, and maintain the air pressure inside the thermal insulation cabin body within the preset pressure range when the air pressure inside the thermal insulation cabin body changes. This greatly reduces the threat of rapid changes in the air pressure inside the thermal insulation cabin body to user safety, and can also play a heat preservation function when the air pressure inside the thermal insulation cabin body is stable.

As an implementation of the embodiment of the present invention, the cryogenic physical therapy cabin may further include a safety module 610, which includes an emergency button arranged inside the thermal insulation cabin body and/or outside the thermal insulation cabin body; the emergency button is electrically connected with the programmable controller 130; the programmable controller 130 is further configured to receive an emergency signal generated when the emergency button is triggered, and perform at least one of the following operations: controlling the refrigeration module 103 to stop refrigeration; controlling the heating module 104 to start heating; and controlling the electrically control cabin door 120 to be opened.

Figure 6A:
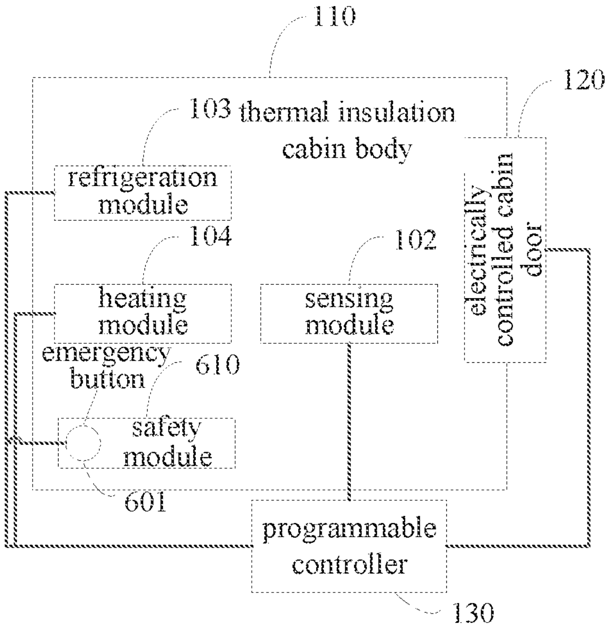
FIG. 6(*a*) is a schematic diagram of a specific structure of a security module based on the embodiment shown in FIG. 1.
Figure 6B:
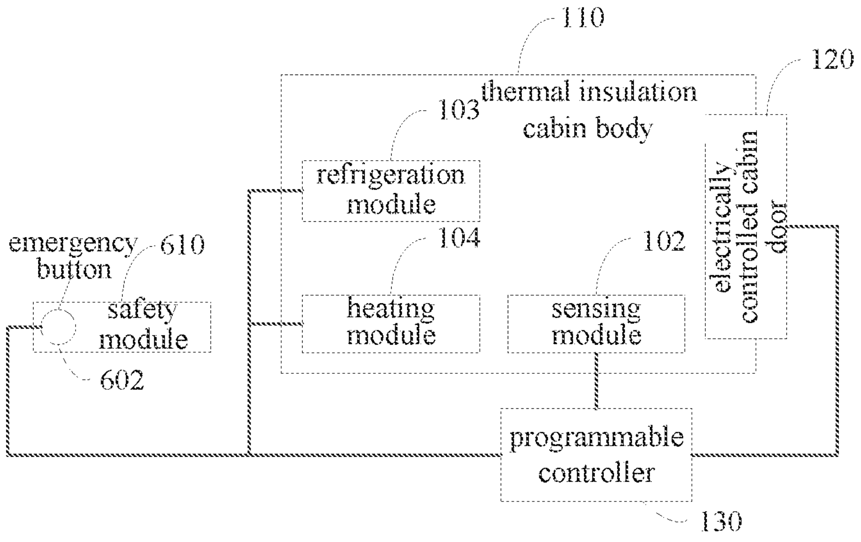
Figure 6C:
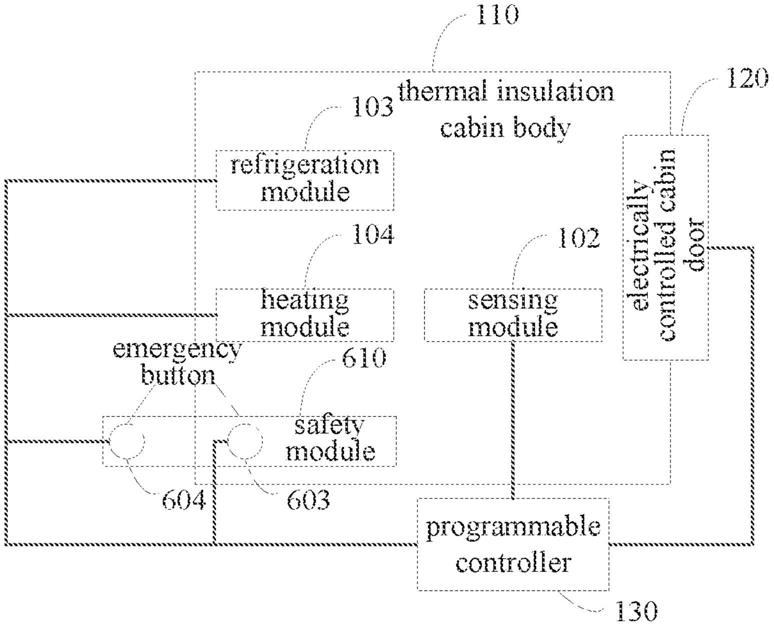

In an implementation, as shown in FIG. 6(*a*), the safety module 610 includes an emergency button 601, which is arranged inside the thermal insulation cabin body 110. The user can press the emergency button 601 arranged inside the thermal insulation cabin body 110 when feeling uncomfortable during cryogenic physical therapy. The programmable controller 130 can receive the emergency signal generated when the emergency button 601 is triggered, and control the refrigeration module 103 to stop refrigerating, the heating module 104 to start heating, and the electronically controlled cabin door 120 to be opened when receiving the emergency signal, such that the internal environmental temperature of the cryogenic physical therapy cabin is increased rapidly to reduce the risk of cryogenic frostbite for user, and the electronically controlled cabin door is opened to allow the user to quickly escape from the internal low-temperature environment of the insulated cabin body 110.

In another implementation, as shown in FIG. 6(*b*), the safety module 610 includes an emergency button 602, which is arranged outside the thermal insulation cabin body 110. During cryogenic physical therapy of the user, other family members can observe conditions inside the cryogenic physical therapy cabin, for example, via a transparent glass observation window of the electronically controlled cabin door 120, or observe via a camera arranged inside the thermal insulation cabin body 110 to obtain a monitoring video during the cryogenic physical therapy of the user in real time. If other family members determine that the user may be experiencing discomfort, or the user has been undergoing cryogenic physical therapy for more than a preset time, they can press the emergency button 602 arranged outside the thermal insulation cabin body 110, so that the programmable controller 130 can receive the emergency signal generated when the emergency button 601 is triggered, and control the refrigeration module 103 to stop refrigeration, the heating module 104 to start heating, and the electronically controlled cabin door 120 to be opened when receiving the emergency signal.

In another implementation, as shown in FIG. 6(*c*), the safety module 610 includes an emergency button 603 and an emergency button 604, wherein the emergency button 603 is arranged inside the thermal insulation cabin body 110 and the emergency button 604 is arranged outside the thermal insulation cabin body 110. Therefore, during cryogenic physical therapy of the user, the user and family members of the user can press the emergency buttons when determining that the user may be in danger, so that the refrigeration module 103 stops refrigeration, the heating module 104 starts heating, and the electrically controlled cabin door 120 is opened, thus further improving the safety of the cryogenic physical therapy process.

It can be seen that in the embodiment, the cryogenic physical therapy cabin further includes the safety module, which includes the emergency button, wherein the emergency button can be arranged inside the thermal insulation cabin body or outside the thermal insulation cabin body, or arranged both inside and outside the thermal insulation cabin body. Therefore, during cryogenic physical therapy of the user, the user and family members of the user can press the emergency button, so that the refrigeration module stops refrigeration, the heating module starts heating, and the electronically controlled cabin door is opened, thereby further improving the safety of the cryogenic physical therapy process and reducing the risk of cryogenic frostbite of the user.

Figure 7:
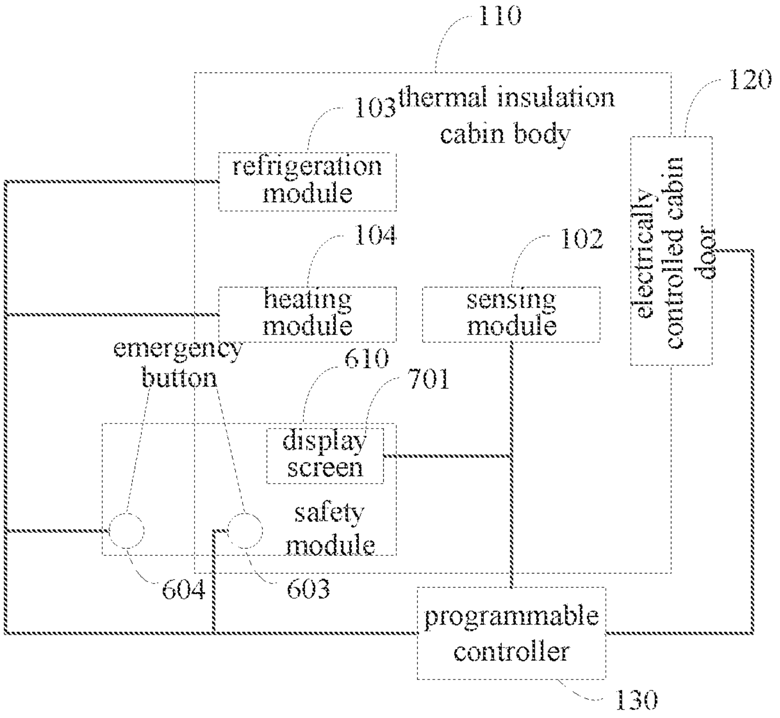
FIG. 7 is a schematic diagram of another specific structure of the security module based on the embodiment shown in FIG. 6(*c*)

As an implementation of the embodiment of the present invention, as shown in FIG. 7, the safety module 610 may further include a display screen 701, which is arranged inside the thermal insulation cabin body 110, and a surface of the display screen is provided with thermal insulation glass, and the display screen 701 is electrically connected with the programmable controller 130; the programmable controller 130 is configured to control the display screen 701 to display safety prompting information when receiving the emergency signal.

The safety module 610 may include the display screen 701, which is arranged inside the thermal insulation cabin body 110, and the surface of the display screen 701 is provided with thermal insulation glass. There may be one or more layers of the thermal insulation glass to isolate temperatures on both sides of the thermal insulation glass, protect the display screen 701 from being affected by the extremely low-temperature environment inside the thermal insulation cabin body 110 and maintain normal display of the display screen 701. Therefore, during the cryogenic physical therapy, if the user or a family member of the user presses the emergency button, the programmable controller 130 can receive the emergency signal generated when the emergency button is triggered, and control the display screen 701 to display the safety prompting information. The safety prompting information may include temperature information inside the thermal insulation cabin body 110, the duration of the cryogenic physical therapy by the user, and other state information, which allows the user to quickly confirm a current state of the cryogenic physical therapy cabin, and then determine a next action.

In an implementation, the safety prompting information may include a process image or video for handling a current emergency situation. For example, the safety prompting information is a video-based operation process of how to force the refrigeration module 103 to stop refrigeration and open the electronically controlled cabin door 120, so that the user can operate according to the video-based operation process displayed on the display screen 701, close the refrigeration module 103 and open the electronically controlled cabin door 120.

In another implementation, emergency supplies such as emergency cotton jackets and the like for dealing with low-temperature environment can be provided inside the thermal insulation cabin body 110, and the safety prompting information displayed on the display screen 701 can include storage location of the emergency supplies, so that the user can obtain emergency supplies for dealing with low-temperature environment based on the storage location. In yet another implementation, the display screen 701 can also be used for the user to have a video conversation with family members or staff in the external environment of the cryogenic physical therapy cabin, so that the user can quickly escape from the low-temperature environment inside the cryogenic physical therapy cabin based on the guidance of the family members or staff.

It can be seen that in the embodiment, the safety module further comprises the display screen, which is arranged inside the thermal insulation cabin body, and the surface of the display screen is provided with thermal insulation glass. The display screen is electrically connected with the programmable controller, so that the programmable controller can control the display screen to display safety prompting information when receiving the emergency signal. By watching the safety prompting information displayed on the display screen, the user can deal with the current emergency and quickly escape from the low-temperature environment in the cryogenic physical therapy cabin according to the safety prompting information, which further reduces the safety risk in the process of cryogenic physical therapy.

Figure 8:
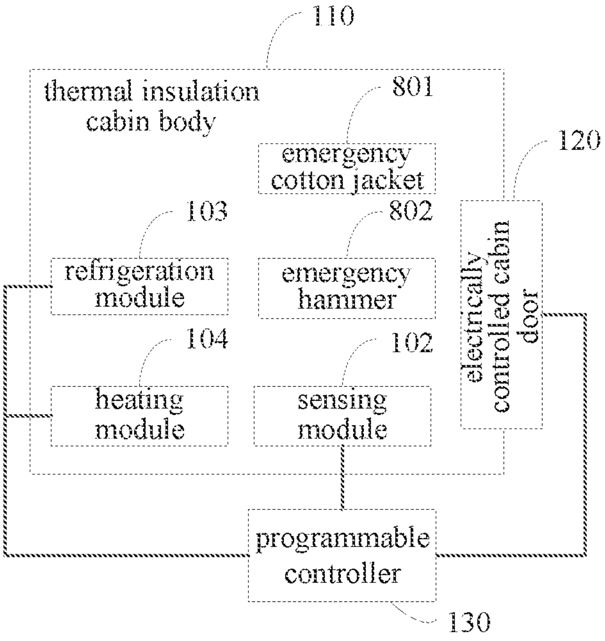
FIG. 8 is a schematic diagram of a configuration of emergency cotton jacket and emergency hammer based on the embodiment shown in FIG. 1.

As an implementation of the embodiment of the present invention, as shown in FIG. 8, an emergency cotton jacket 801 and an emergency hammer 802 can also be arranged inside the above thermal insulation cabin body 110.

In an implementation, the emergency cotton jacket 801 and the emergency hammer 802 are also arranged inside the thermal insulation cabin body 110. When a user feels uncomfortable in the process of, The user can press the emergency button arranged inside the thermal insulation cabin body 110 when feeling uncomfortable during cryogenic physical therapy. If the programmable controller 130 fails to respond to the emergency signal generated when the emergency button is triggered, or the electronically controlled cabin door cannot be opened, it is difficult for the user to escape from the interior of the cryogenic physical therapy cabin, and staying in the cryogenic physical therapy cabin for a long time may cause damage to the user's health. Therefore, the user can quickly escape from the cryogenic physical therapy cabin by using the emergency cotton coat 801 and the emergency hammer 802. For example, a user can put on the emergency cotton jacket 801 to avoid cryogenic frostbite, and use the emergency hammer 802 to hit a glass area of the electronically controlled cabin door 120 to break the glass, so that the internal and external environment of the thermal insulation cabin body 110 can circulate, and then the temperature inside the thermal insulation cabin body 110 can be rapidly increased, and the user can also quickly escape from the interior of the cryogenic physical therapy cabin.

It can be seen that in the embodiment, the emergency cotton jacket and the emergency hammer can also be arranged inside the thermal insulation cabin body 110, so that when the programmable controller fails to respond to the emergency signal or the electronically controlled cabin door cannot be opened, the user can quickly escape from the cryogenic physical therapy cabin by using the emergency cotton jacket and the emergency hammer, which reduces the safety risk in the process of cryogenic physical therapy.

Figure 9:
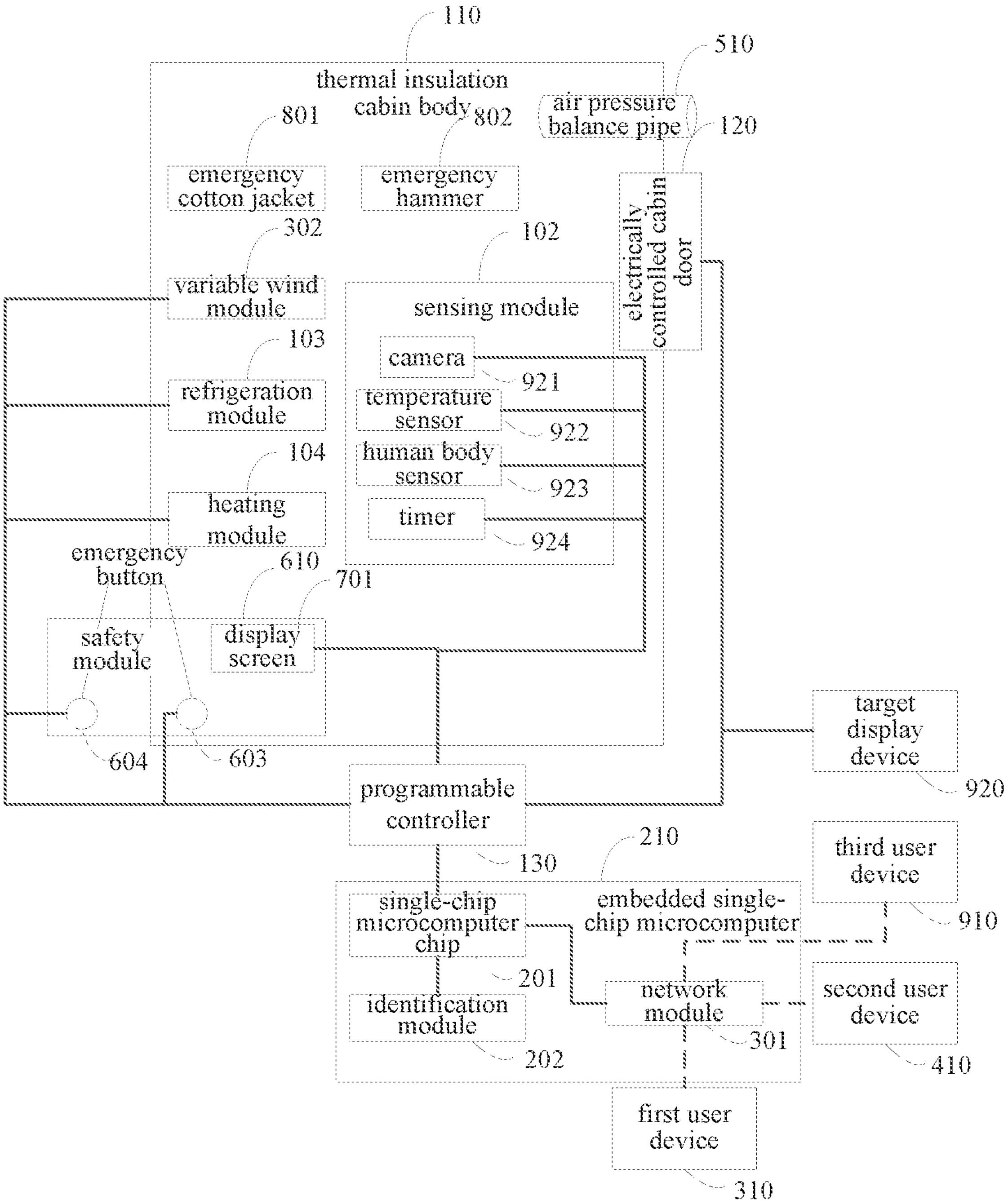
FIG. 9 is a schematic diagram of another specific structure of the cryogenic physical therapy cabin for home use based on the embodiment shown in FIG. 1.

As an implementation of the embodiment of the present invention, as shown in FIG. 9, the sensing module 102 may include a camera 921, a temperature sensor 922, a human body sensor 923 and a timer 924; the camera 921 is configured to acquire a monitoring video inside the thermal insulation cabin body 110 and send the monitoring video to the programmable controller 130. The temperature sensor 922 is configured to acquire temperature data inside the thermal insulation cabin body 110 and send the temperature data to the programmable controller 130. The human body sensor 923 is configured to detect human body data inside the thermal insulation cabin body and send the human body data to the programmable controller 130. The programmable controller 130 is configured to send the monitoring video to a third user device 910 and/or control a target display device 920 to play the monitoring video. The programmable controller 130 is further configured to control the timer 924 to start timing when determining that there is a person inside the thermal insulation cabin body 110 based on the human body data, and to control the electrically controlled door 120 to be closes when determining that there is no person inside the thermal insulation cabin body 110 based on the human body data. The programmable controller 130 is further configured to perform, when determining that the temperature inside the thermal insulation cabin body 110 is lower than a preset threshold based on the temperature data or when the timing duration of the timer 924 reaches a preset duration, at least one of controlling the refrigeration module 103 to stop refrigeration, controlling the heating module 104 to start heating, and controlling the electrically control cabin door 120 to be opened.

The sensing module 102 includes the camera 921, the temperature sensor 922, the human body sensor 923 and the timer 924. In an implementation, the camera 921 can acquire the monitoring video inside the thermal insulation cabin body 110, and send the monitoring video to the programmable controller 130, so that the programmable controller 130 can send the monitoring video to the third user device 910, which can be an intelligent device of the emergency contact of the user, such as a portable electronic device such as the mobile phone, and can also be a monitoring device of the manufacturer of the cryogenic physical therapy cabin, etc., which is not specifically limited here. Therefore, the emergency contact of the user or the staff of the manufacturer of the cryogenic physical therapy cabin can watch the received monitoring video, to improve the safety in the process of cryogenic physical therapy of the user. The programmable controller 130 can also control the target display device 920 to play the monitoring video. The target display device 920 can be a display screen and other display devices arranged outside the thermal insulation cabin body 110, and other family members of the user can watch the monitoring video played by the target display device 920 to determine whether the user is safe in the process of cryogenic physical therapy. The programmable controller 130 can also send the monitoring video to the third user device 910 and control the target display device 920 to play the monitoring video, thus further improving the safety of cryogenic physical therapy.

In an implementation, the temperature sensor 922 can acquire the temperature data inside the thermal insulation cabin body 110 and send the temperature data to the programmable controller 130. The human body sensor 923 can detect the human body data inside the thermal insulation cabin body 110 and send the human body data to the programmable controller 130. Therefore, based on the acquired temperature data and human body data, the programmable controller 130 can control the refrigeration module 103 to stop refrigerating, control the heating module 104 to start heating, or control the electrically controlled door 120 to be opened when the temperature inside the thermal insulation cabin body 110 is lower than the preset threshold and the human body data indicates that there is a user inside the thermal insulation cabin body 110, which prevents the user from being frostbitten by extremely low temperature. The programmable controller 130 can also control the electronically controlled cabin door 120 to be closed when determining that there is no person inside the thermal insulation cabin body based on the acquired human body data, thus preventing strangers or children from entering the cryogenic physical therapy cabin by mistake, which can cause danger.

In an implementation, the programmable controller 130 can control the timer 924 to start timing when determining that there is a person inside the thermal insulation cabin body 110 based on the acquired human body data, and can control the refrigeration module 103 to stop refrigeration, the heating module 104 to start heating, or the electrically controlled cabin door 120 to be opened when the timing duration of the timer reaches a preset duration, thus avoiding the risk of frostbite caused by the user being in a low-temperature environment for a long time.

It can be seen that in the embodiment, the sensing module can include a camera, a temperature sensor, a human body sensor and a timer. The programmable controller can send the monitoring video of the interior of the thermal insulation cabin body collected by the camera to the third user device, and can also control the target display device to play the monitoring video, further improving the safety of cryogenic physical therapy. The programmable controller can also control the timer to start timing when determining that there is a person inside the thermal insulation cabin body based on the human body data detected by the human body sensor, and control the electronically controlled cabin door to be closes when determining that there is no person inside the thermal insulation cabin body based on the human body data, thus avoiding strangers or children from entering the cryogenic physical therapy cabin by mistake, which can cause danger. When the timing duration of the timer reaches the preset duration, or the temperature inside the thermal insulation cabin body indicated by the temperature data collected by the temperature sensor is lower than the preset threshold, the programmable controller can control the refrigeration module to stop refrigeration, the heating module to start heating, or the electronically controlled cabin door to be opened, thus avoiding the risk of frostbite caused by the user being in an extremely low-temperature environment or being in a low-temperature environment for a long time.

The specific structure of the cryogenic physical therapy cabin is descripted in the following in combined with the schematic structure diagram of the cryogenic physical therapy cabin for home use shown in FIG. 9. The cryogenic physical therapy cabin provided by embodiments of the present invention includes the thermal insulation cabin body 110, the electrically controlled cabin door 120, the sensing module 102, the refrigeration module 103, the heating module 104 and the programmable controller 130. The sensing module 102, the refrigeration module 103, the heating module 104 and the variable wind module 302 are arranged inside the thermal insulation cabin body 110, and the emergency cotton jacket 801 and the emergency hammer 802 are also arranged inside the thermal insulation cabin body 110. The programmable controller 130 is electrically connected with the sensing module 102, the refrigeration module 103, the heating module 104, the electrically controlled cabin door 120 and the variable wind module 302, respectively. The sensing module 102 includes the camera 921, the temperature sensor 922, the human body sensor 923 and the timer 924, and can acquire the sensing data inside the thermal insulation cabin body 110 and send the sensing data to the programmable controller 130.

The cryogenic physical therapy cabin is also provided with the embedded single-chip microcomputer 210, which includes the single-chip microcomputer chip 201, the identification module 202 and the network module 301, and the single-chip microcomputer chip 201 is electrically connected with the identification module 202, the network module 301 and the programmable controller 130 respectively. The identification module 202 can acquire the biometric information of the user, so that the single-chip microcomputer chip 201 can determine whether the biometric information matches the pre-stored feature information, and then determine whether to generate a door opening signal.

The network module 301 is communicatively connected to the first user device 310, the second user device 410 and the third user device 910 respectively. The network module 301 can acquire the operation information input by the first user device 310; the network module 301 can also send a prompt message to the second user device 410, and the prompt message is generated by the single-chip microcomputer chip 201 based on the abnormal information acquired by the programmable controller 130; the network module 301 can also send the monitoring video inside the thermal insulation cabin body 110 acquired by the camera 921 to the third user device 910.

The programmable controller 130 can, based on the operation instruction issued by the single-chip microcomputer chip 201 and/or the sensing data acquired by the sensing module 102, control the opening and closing of the electronically controlled cabin door 120, and control the refrigeration module 103 to refrigerate, the heating module 104 to heat, and the variable wind module 302 to adjust the wind speed.

The cryogenic physical therapy cabin is also provided with the air pressure balance pipe 510, which connects the internal environment with external environment of the thermal insulation cabin body 110. The air pressure balance pipe 510 can maintain the air pressure inside the thermal insulation cabin body 110 within the preset pressure range when the air pressure inside the thermal insulation cabin body 110 changes.

The cryogenic physical therapy cabin is also provided with the safety module 610, which includes the display screen 701 arranged inside the thermal insulation cabin body 110. The safety module 610 also includes emergency buttons, including the emergency button 603 arranged inside the thermal insulation cabin body 110 and the emergency button 604 arranged outside the thermal insulation cabin body 110. The programmable controller 130 is electrically connected with the emergency button 603, the emergency button 604 and the display screen 701. By pressing the emergency button 603 or the emergency button 604, the programmable controller 130 can receive an emergency signal generated when the emergency button is triggered, and thus control the display screen 701 to display the safety prompting information and performing at least one of controlling the refrigeration module 103 to stop refrigeration; controlling the heating module 104 to start heating and controlling the electronically controlled cabin door 120 to be opened.

The cryogenic physical therapy cabin is also provided with the target display device 920. The programmable controller 130 can control the target display device 920 to play the monitoring video of the interior of the thermal insulation cabin body 110 acquired by the camera 921.

It can be seen that the cryogenic physical therapy cabin for home use provided by embodiments of the present invention supports to be operated by a single user, thus meeting home cryogenic physical therapy needs of the user; and also effectively reduces the safety risk of cryogenic physical therapy, and facilitates the manufacturer of the cryogenic physical therapy cabin to obtain the diagnostic information for maintenance; and further supports configuring various cryogenic physical therapy schemes for different users, and supports configuring the cryogenic physical therapy cabin remotely by the user, thus better meeting cryogenic physical therapy needs of the user.

It should be noted that relational terms such as first and second and the like herein are only used to distinguish one entity or operation from another and do not necessarily require or imply any such actual relationship or order between these entities or operations. Moreover, the terms “comprising”, “including” or any other variations thereof are intended to encompass a non-exclusive inclusion such that a process, method, article or device that includes a series of elements includes not only those elements, but also includes other elements not explicitly listed or other elements inherent to such a process, method, article or apparatus. Without further limitation, elements defined by the phrase “comprising one . . . ” do not preclude the presence of additional identical elements in a process, method, article or device that includes the mentioned elements.

The various embodiments in this specification are described in a related manner Each embodiment focuses on the differences from other embodiments, and the same and similar parts between the various embodiments can be referred to each other. The above descriptions are only preferred embodiments of the invention, and are not intended to limit the scope of protection of the invention. Any modifications, equivalent replacements, improvements and the like made within the spirit and principles of the disclosure shall be included within the scope of protection of the invention.

The invention claimed is:

1. A cryogenic physical therapy cabin for home use, wherein the cryogenic physical therapy cabin comprises a thermal insulation cabin body, an electronically controlled cabin door, a sensing module, a refrigeration apparatus for reducing a temperature inside the cryogenic physical therapy cabin, a heating apparatus for rapidly increasing the temperature inside the cryogenic physical therapy cabin and a programmable controller, wherein:

the sensing module, the refrigeration apparatus and the heating apparatus are arranged inside the thermal insulation cabin body, and the programmable controller is electrically connected with the sensing module, the refrigeration apparatus, the heating apparatus and the electrically controlled cabin door respectively;

the sensing module is configured to acquire sensing data and send the sensing data to the programmable controller; and the programmable controller is configured to control opening and closing of the electronically controlled cabin door based on an operation instruction issued by a first user and/or the sensing data; and the programmable controller is further configured to control the refrigeration apparatus to perform a refrigeration operation and control the heating apparatus to perform a heating operation based on the sensing data;

wherein the cryogenic physical therapy cabin further comprises an air pressure balance pipe, and the air pressure balance pipe connects an internal environment with an external environment of the thermal insulation cabin body; and the air pressure balance pipe is configured to maintain air pressure inside the thermal insulation cabin body within a preset pressure range when the air pressure inside the thermal insulation cabin body changes.

2. The cryogenic physical therapy cabin according to claim 1, wherein the cryogenic physical therapy cabin further comprises an embedded single-chip microcomputer, which comprises a single-chip microcomputer chip and an identification module, wherein:

the single-chip microcomputer chip is electrically connected with the identification module and the programmable controller respectively;

the identification module is configured to acquire biometric information of a user; and the single-chip microcomputer chip is configured to generate a cabin door opening signal when determining that the biometric information matches pre-stored feature information, and send the cabin door opening signal to the programmable controller; and the programmable controller is configured to control the electronically controlled cabin door to be opened when receiving the cabin door opening signal.

3. The cryogenic physical therapy cabin according to claim 2, wherein the cryogenic physical therapy cabin further comprises a variable wind module, which is electrically connected with the programmable controller, and the embedded single-chip microcomputer further comprises a network module, wherein the single-chip microcomputer chip is electrically connected with the network module and the programmable controller respectively, and the network module establishes a communication connection with a first electronic device;

the network module is configured to acquire first operation information input by a second user via the first electronic device, and send the first operation information to the single-chip microcomputer chip, wherein the first operation information comprises at least one of start time, temperature and wind speed;

the single-chip microcomputer chip is configured to generate a first control instruction based on the first operation information and send the first control instruction to the programmable controller; and the programmable controller is configured to control a target component in the cryogenic physical therapy cabin to perform an operation indicated by the first control instruction when receiving the first control instruction, wherein the target component comprises at least one of the refrigeration apparatus, the heating apparatus, the electrically controlled cabin door and the variable wind module.

4. The cryogenic physical therapy cabin according to claim 3, wherein the network module establishes a communication connection with a second electronic device;

the programmable controller is further configured to determine whether an abnormal situation occurs in the cryogenic physical therapy cabin based on a device state of the cryogenic physical therapy cabin, and send abnormal information to the single-chip microcomputer chip if the abnormal situation occurs in the cryogenic physical therapy cabin; and the single-chip microcomputer chip is configured to generate a prompt message based on the abnormal information and send the prompt message to the second electronic device through the network module;

wherein the abnormal situation includes: the electronically controlled cabin door of the cryogenic physical therapy cabin being not opened, and a circuit of the cryogenic physical therapy cabin being faulty.

5. The cryogenic physical therapy cabin according to claim 1, wherein the cryogenic physical therapy cabin further comprises a safety module, wherein the safety module comprises an emergency button, and the emergency button is arranged inside the thermal insulation cabin body and/or outside the thermal insulation cabin body; the emergency button is electrically connected with the programmable controller; and the programmable controller is further configured to receive an emergency signal generated when the emergency button is triggered, and perform at least one of:

controlling the refrigeration apparatus to stop refrigeration, controlling the heating module heating apparatus to start heating, and controlling the electronically controlled cabin door to be opened.

6. The cryogenic physical therapy cabin according to claim 5, wherein the safety module further comprises a display screen, wherein the display screen is arranged inside the thermal insulation cabin body, and a surface of the display screen is provided with thermal insulation glass, and the display screen is electrically connected with the programmable controller; and the programmable controller is configured to control the display screen to display safety prompt information when receiving the emergency signal.

7. The cryogenic physical therapy cabin according to claim 1, wherein the sensing module comprises a camera, a temperature sensor, a human body sensor and a timer;

the camera is configured to acquire a monitoring video inside the thermal insulation cabin body and send the monitoring video to the programmable controller; the temperature sensor is configured to acquire temperature data inside the thermal insulation cabin body and send the temperature data to the programmable controller; the human body sensor is configured to detect human body data inside the thermal insulation cabin body and send the human body data to the programmable controller;

the programmable controller is configured to send the monitoring video to a third electronic device and/or control a target display screen to play the monitoring video;

the programmable controller is further configured to control the timer to start timing when determining that there is a person inside the thermal insulation cabin body based on the human body data, and control the electronically controlled cabin door to be closed when determining that there is no person inside the thermal insulation cabin body based on the human body data; and the programmable controller is further configured to perform, when determining that a temperature inside the thermal insulation cabin body is lower than a preset threshold based on the temperature data or when timing duration of the timer reaches a preset duration, at least one of controlling the refrigeration apparatus to stop refrigeration, controlling the heating apparatus to start heating, and controlling the electronically controlled cabin door to be opened.

* * * * *